United States Patent
Chakraborty et al.

(10) Patent No.: US 10,266,467 B2
(45) Date of Patent: *Apr. 23, 2019

(54) SYNTHESIS OF GLYCOLS VIA TRANSFER HYDROGENATION OF ALPHA-FUNCTIONAL ESTERS WITH ALCOHOLS

(71) Applicant: Eastman Chemical Company, Kingsport, TN (US)

(72) Inventors: Sumit Chakraborty, Johnson City, TN (US); Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,320

(22) Filed: Jul. 24, 2018

(65) Prior Publication Data

US 2019/0039978 A1 Feb. 7, 2019

Related U.S. Application Data

(60) Provisional application No. 62/540,354, filed on Aug. 2, 2017.

(51) Int. Cl.

| | | |
|---|---|---|
| *C07C 29/00* | (2006.01) | |
| *C07F 15/00* | (2006.01) | |
| *B01J 31/00* | (2006.01) | |
| *C07C 29/128* | (2006.01) | |
| *B01J 31/24* | (2006.01) | |
| *C07F 15/02* | (2006.01) | |
| *B01J 31/18* | (2006.01) | |
| *B01J 31/20* | (2006.01) | |
| *C07C 29/147* | (2006.01) | |
| *B01J 31/02* | (2006.01) | |

(52) U.S. Cl.
CPC ......... *C07C 29/1285* (2013.01); *B01J 31/189* (2013.01); *B01J 31/20* (2013.01); *B01J 31/24* (2013.01); *C07C 29/147* (2013.01); *C07F 15/025* (2013.01); *B01J 31/0202* (2013.01); *B01J 2231/641* (2013.01); *B01J 2231/643* (2013.01); *B01J 2531/0244* (2013.01); *B01J 2531/842* (2013.01)

(58) Field of Classification Search
CPC .... C07F 15/02; C07F 15/025; C07C 29/1285; B01J 31/24
See application file for complete search history.

(56) References Cited

U.S. PATENT DOCUMENTS

| | | |
|---|---|---|
| 1,400,195 A | 12/1921 | Willkie |
| 1,857,921 A | 5/1932 | Lazier |
| 1,999,403 A | 4/1935 | Dreyfus |
| 2,060,880 A | 11/1936 | Lazier |
| 2,152,182 A | 3/1939 | Ellis et al. |
| 2,305,104 A | 12/1942 | Pardee, Jr. |
| 2,504,497 A | 4/1950 | Charles et al. |
| 2,607,805 A | 8/1952 | Gresham |
| 3,911,003 A | 10/1975 | Suzuki |
| 4,052,424 A | 10/1977 | Vanderspurt |
| 4,076,594 A | 2/1978 | Buelow et al. |
| 4,112,245 A | 9/1978 | Zehner et al. |
| 4,149,009 A | 4/1979 | Yoneoka et al. |
| 4,214,106 A | 7/1980 | Freudenberger et al. |
| 4,216,339 A | 8/1980 | Couteau et al. |
| 4,217,460 A | 8/1980 | Hohenschutz et al. |
| 4,218,568 A | 8/1980 | Hohenschutz et al. |
| 4,232,171 A | 11/1980 | Yoneoka et al. |
| 4,319,037 A | 3/1982 | Yoneoka |
| 4,326,073 A | 4/1982 | Wolf et al. |
| 4,366,333 A | 12/1982 | Wilkes |
| 4,436,835 A | 3/1984 | Horie et al. |
| 4,440,873 A | 4/1984 | Miyazaki et al. |
| 4,453,026 A | 6/1984 | Tahara et al. |
| 4,480,122 A | 10/1984 | Horlenko et al. |
| 4,511,744 A | 4/1985 | Miyazaki et al. |

(Continued)

FOREIGN PATENT DOCUMENTS

| | | |
|---|---|---|
| CA | 1 238 919 A | 7/1988 |
| EP | 2 599 544 A1 | 6/2013 |

(Continued)

OTHER PUBLICATIONS

Monnereau et al. Efficient Synthesis of Differentiated syn-1,2-Diol Derivatives by Asymmetric Transfer Hyrogenation-Dynamic Kinetic Resolution of U + 03 B1-Alkoxy-Substituted U +03B2—Ketoesters. Chemistry—A European Journal, vol. 21 (33), 11799-11806. (Year: 2015).*

Kim et al. Transfer Hydrogenation of Organic Formates and Cyclic Carbonates: An Alternative Route to Methanol from Carbon Dioxide. Catalysis, vol. 4, 3630-3636. (Year: 2014).*

Patil et al. Immobilized Iron Metal-Containing Ionic Liquid-Catalyzed Chemoselective Transfer Hydrogenation of Nitroarenes into Anilines. Sustainable Chemistry & Engineering, vol. 4, 429-436. (Year: 2016).*

Co-pending U.S. Appl. No. 16/043,303, filed Jul. 24, 2018; Chakraborty et al.

(Continued)

*Primary Examiner* — Sikarl A Witherspoon
(74) *Attorney, Agent, or Firm* — Matthew W. Smith

(57) ABSTRACT

A transfer hydrogenation process for forming vicinal diols by hydrogenating 1,2-dioxygenated organic compounds using alcohols as the reducing agent instead of the traditional $H_2$ gas. The transfer hydrogenation is carried out under milder conditions of temperature and pressure than is typical for ester hydrogenation with $H_2$. The milder conditions of operation provide benefits, such as lower operating and capital costs for industrial scale production as well as savings in product purification due to the avoidance of by-products from exposure of reaction mixtures and products to high temperatures.

24 Claims, No Drawings

(56) References Cited

U.S. PATENT DOCUMENTS

| | | | |
|---|---|---|---|
| 4,601,909 | A | 7/1986 | Nagoshi |
| 4,677,234 | A | 6/1987 | Bartley |
| 4,792,620 | A | 12/1988 | Paulik et al. |
| 5,144,062 | A | 9/1992 | Chen et al. |
| 5,194,675 | A | 3/1993 | Joerg et al. |
| 5,206,433 | A | 4/1993 | Hohenschutz et al. |
| 6,376,723 | B2 | 4/2002 | Drent et al. |
| 6,455,742 | B1 | 9/2002 | Cortright et al. |
| 6,841,085 | B2 | 1/2005 | Werpy et al. |
| 6,956,134 | B2 | 10/2005 | Liu et al. |
| 7,615,671 | B2 | 11/2009 | Puckette et al. |
| 8,455,677 | B2 | 6/2013 | Nakamura et al. |
| 8,969,632 | B2 | 3/2015 | Norman et al. |
| 9,040,748 | B2 | 5/2015 | Janka et al. |
| 9,493,395 | B2 | 11/2016 | Janka et al. |
| 2015/0151289 | A1* | 6/2015 | Mikhailine ............ C07C 29/145 546/344 |
| 2015/0274621 | A1 | 10/2015 | Fairweather et al. |
| 2016/0318956 | A1* | 11/2016 | Quintaine ............. C07F 9/5004 |
| 2016/0326202 | A1* | 11/2016 | Morris ................... B01J 31/189 |

FOREIGN PATENT DOCUMENTS

| | | |
|---|---|---|
| GB | 2 116 552 A | 9/1983 |
| WO | WO 82/03854 A1 | 11/1982 |
| WO | WO 2006/106483 A1 | 10/2006 |
| WO | WO 2006/106484 A1 | 10/2006 |
| WO | WO 2013/079659 A1 | 6/2013 |
| WO | WO 2015/091158 A1 | 6/2015 |
| WO | WO-2017194663 A1 * | 11/2017 |

OTHER PUBLICATIONS

Co-pending U.S. Appl. No. 16/043,308, filed Jul. 24, 2018; Chakraborty et al.
Office Action dated Oct. 9, 2018, received in co-pending U.S. Appl. No. 16/043,308.
Co-pending U.S. Appl. No. 16/043,312, filed Jul. 24, 2018; Chakraborty et al.
Co-pending U.S. Appl. No. 16/043,317, filed Jul. 24, 2018; Chakraborty et al.
Co-pending U.S. Appl. No. 16/043,324, filed Jul. 24, 2018; Barnicki et al.
Co-pending U.S. Appl. No. 16/043,329, filed Jul. 24, 2018; Barnicki et al.
Wittstock et al.; "Nanoporous Gold Catalysts for Selective Gas-Phase Oxidative Coupling of Methanol at Low Temperature;" Science; 2010; vol. 327; pp. 319-323.
Wang et al.; "Graphene-supported Au—Pd bimetallic nanoparticles with excellent catalytic performance in selective oxidation of methanol to methyl formate;" Chem. Commun., 2013, 49, pp. 8250-8252.
Liu et al.; "Methanol Selective Oxidation to Methyl Formate over $ReO_x/CeO_2$ Catalysts;" Catal. Lett.; 2008; 120; pp. 274-280.
Huang et al.; "Effect of treatment temperature on structures and properties of zirconia-supported ruthenium oxide catalysts for selective oxidation of methanol to methyl formate;" Catalysis Today; 2012; 183; pp. 58-64.
Kaichev et al.; "Selective oxidation of methanol to form dimethoxymethane and methyl formate over a monolayer $V_2O_5/TiO_2$ catalystr;" Journal of Catalysis; 2014; 311; pp. 59-70.
Itagaki et al.; "Transition Metal Homogeneous Catalysis for Liquid-Phase Dehydrogenation of Methanol;" Journal of Molecular Catalysis; 1987; 41; pp. 209-220.
Smith et al.; "The Ruthenium-Catalysed Conversion of Methanol into Methyl Formate;" Journal of Organometallic Chemistry; 1985; 291; pp. C13-C14.
Yang et al.; "Mechanistic study on dehydrogenation of methanol with $[RuCl_2(PR_3)_3]$-type catalyst in homogeneous solutions;" Journal of Molecular Catalysis A: Chemical; 1996; 108; pp. 87-93.
Yamakawa et al.; "Catalytic Reaction of Methanol with a Series of Ruthenium (II) Complexes and the Mechanism of the Formation of Acetic Acid from Methanol Alone;" J. Chem. Soc. Dalton Trans.; 1994; pp. 2265-2269.
Shinoda et al.; "One-step Formation of Methyl Acetate with Methanol used as the Sole Source and Catalysis by Ru"—Sn" Cluster Complexes;" J. Chem. Soc., Chem. Commun.; 1990; pp. 1511-1512.
Kuriyama et al.; "Catalytic Hydrogenation of Esters. Development of an Efficient Catalyst and Processes for Synthesising (R)-1,2-Propanediol and 2-(I-Menthoxy)ethanol;" Org. ProcessRes. Dev.; 2012; 16; pp. 166-171.
Liu et al.; "Towards a Sustainable Synthesis of Formate Salts: Combined Catalytic Methanol Dehydrogenation and Bicarbonate Hydrogenation;" Angew. Chem. Int. Ed.; 2014; 53; pp. 7085-7088.
Alberico et al.; "Selective Hydrogen Production from Methanol with a Defined Iron Pincer Catalyst under Mild Conditions;" Angew. Chem. Int. Ed.; 2013; 52; pp. 14162-14166.
Werkmeister et al.; "Pincer-Type Complexes for Catalytic (De)Hydrogenation and Transfer (De)Hydrogenation Reactions: Recent Progress;" Chem. Eur. J.; 2015; 21; pp. 12226-12250.
Chakraborty et al.; "Nickel and Iron Pincer Complexes as Catalysts for the Reduction of Carbonyl Compounds;" Acc. Chem. Res.; 2015; 48; pp. 1995-2003.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Structure of $\eta^4$-$Ph_4C_4CO$)(CO)$_3$Ru—a Catalyst Precursor in H-Transfer and Dehydrogenation Reactions of Alcohols;" Inorganica Chimica Acta; 1985; 97; pp. L25-L26.
Warner et al.; "Shvo's Catalyst in Hydrogen Transfer Reactions;" Top Organomet Chem; 2011; 37; pp. 85-125.
Zhang et al.; "Facile Conversion of Alcohols into Esters and Dihydrogen Catalyzed by New Ruthenium Complexes;" J. Am. Chem. Soc.; 2005; 127; pp. 10840-10841.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.
Chakraborty et al.; "A Molecular Iron Catalyst for the Acceptorless Dehydrogenation and Hydrogenation of N-Heterocycles;" J. Am. Chem. Soc.; 2014; 136; pp. 8564-8567.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Chakraborty et al.; "Iron-Based Catalysts for the Hydrogenation of Esters to Alcohols;" J. Am. Chem. Soc.; 2014; 136; pp. 7869-7872.
Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.
Hu et al.; "Rechargeable Hydrogen Storage System Based on the Dehydrogenative Coupling of Ethylenediamine with Ethanol;" Angew. Chem. Int. Ed.; 2016; 55; pp. 1061-1064.
Kim et al.; "Ruthenium-Catalyzed Urea Synthesis Using Methanol as the C1 Source;" Org. Lett.; 2016; 18; pp. 212-215.
Crabtree, Robert H.; "Resolving Heterogeneity Problems and Impurity Artifacts in Operationally Homogeneous Transition Metal Catalysts;" Chem. Rev.; 2012; 112; pp. 1536-1554.
Gnanadesikan et al.; "Direct Catalytic Asymmetric Aldol-Tishchenko Reaction;" J. Am. Chem. Soc.; 2004; 126; pp. 7782-7783.
Haslam, Edwin; "Tetrahedron Report No. 93—Recent Developments in Methods for the Esterification and Protection of the Carboxyl Group;" Tetrahedron; 1980; vol. 36; pp. 2409-2433.
Gregory et al.; "The Production of Ethyl Acetate From Ethylene and Acetic Acid Using Clay Catalysts;" Clay Minerals; 1983; 18; pp. 431-435.
Goldemberg, José; "Ethanol for a Sustainable Energy Future;" Science; 2007; vol. 315; pp. 808-810.

(56) References Cited

OTHER PUBLICATIONS

Wang et al.; "Direct transformation of ethanol to ethyl acetate on Cu/ZrO2 catalyst" Reac. Kinet. Mech. Cat.; 2010; 101; pp. 365-375.
Inui et al.; "Effective formation of ethyl acetate from ethanol over Cu—Zn—Zr—Al—O catalyst;" Journarl of Molecular Catalysis A: Chemical; 2004; 216; pp. 147-156.
Zonetti et al.; "Chemicals from ethanol—The dehydrogenative route of the ethyl acetate one-pot synthesis;" Journal of Molecular Catalysis A: Chemical; 2011; 334; pp. 29-34.
Medeiros et al.; "The role of water in ethanol oxidation over SnO2-supported molybdenum oxides;" Catalysis Letters; 69; 2000; pp. 79-82.
Gunanathan et al.; "Applications of Acceptorless Dehydrogenation and Related Transformations in Chemical Synthesis;" Science; 2013; vol. 341; pp. 249.
Bertoli et al.; "Osmium and Ruthenium Catalysts for Dehydrogenation of Alcohols;" Organometallics; 2011; 30; pp. 3479-3482.
Nielsen et al.; "Efficient Hydrogen Production from Alcohols under Mild Reaction Conditions;" Angew. Chem. Int. Ed.; 2011; 50; pp. 9593-9597.
Morton et al.; "Molecular Hydrogen Complexes in Catalysis: Highly Efficient Hydrogen Production from Alcoholic Substrates catalyzed by Ruthenium Complexes;" J. Chem. Soc., Chem. Commun.; 1988; pp. 1154-1156.
Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.
Carlini et al.; "Selective synthesis of isobutanol by means of the Guerbet reaction Part 2. Reaction of methanol/ethanol and methanol/ethanol/n-propanol mixtures over copper based/MeONa catalytic systems;" Journal of Molecular Catalysis A: Chemical; 200; 2003; pp. 137-146.
Furukawa et al.; "High Polymerization of Acetaldehyde by Alumina—A New Method of Preparation of Polyether;" Journal of Polymer Science; vol. XXXVI; Issue No. 130; 1959; pp. 546.
Degering et al.; "Polymerization of Acetaldehyde and Crotonaldehyde Catalyzed by Aliphatic Tertiary Amines;" Journal of Polymer Science; vol. VII; No. 6; pp. 653-656.
Teunissen et al.; "Ruthenium catalyzed hydrogenation of dimethyl oxalate to ethylene glycol;" Chem. Commun.; 1997; pp. 667-668.
Zhang et al.; "Efficient Homogeneous Catalytic Hydrogenation of Esters to Alcohols;" Angew. Chem. Int. Ed.; 2006; 45; pp. 1113-1115.
Saudan et al.; "Dihydrogen Reduction of Carboxylic Esters to Alcohols under the Catalysis of Homogeneous Ruthenium Complexes: High Efficiency and Unprecedented Chemoselectivity;" Angew. Chem. Int. Ed.; 2007; 46; pp. 7473-7476.
Dub et al.; "Catalytic Reductive Transformations of Carboxylic and Carbonic Acid Derivatives Using Molecular Hydrogen;" ACS Catal.; 2012; 2; pp. 1718-1741.
Clarke, Matthew L.; "Recent developments in the homogeneous hydrogenation of carboxylic acid esters;" Catal. Sci. Technol.; 2012; 2; pp. 2418-2423.
Chakraborty et al.; "First-row transition metal catalyzed reduction of carbonyl functionalities: a mechanistic perspective;" Dalton Trans.; 2010; 39; pp. 7427-7436.
Zell et al.; "Unprecedented Iron-Catalyzed Ester Hydrogenation. Mild, Selective, and Efficient Hydrogenation of Trifluoroacetic Esters to Alcohols Catalyzed by an Iron Pincer Complex;" Angew. Chem. Int. Ed.; 2014; 53; pp. 4685-4689.
Werkmeister et al.; "Hydrogenation of Esters to Alcohols with a Well-Defined Iron Complex;" Angew. Chem. Int. Ed.; 2014; 53; pp. 8722-8726.
Wang et al.; "The Golden Age of Transfer Hydrogenation;" Chem. Rev.; 2015; 115; pp. 6621-6686.
Lee et al.; "Transfer Hydrogenation of Ketones, Nitriles, and Esters Catalyzed by a Half-Sandwich Complex of Ruthenium;" ChemCatChem; 2015; 7; pp. 107-113.
Dubey et al.; "Catalytic Ester Metathesis Reaction and Its Application to Transfer Hydrogenation of Esters;" ACS Catal.; Jun. 2016; pp. 3998-4002.
Dusselier et al.; "Lactic acid as a platform chemical in the biobased economy: the role of chemocatalysis;" Energy Environ. Sci.; 2013; 6; pp. 1415-1442.
Carnahan et al.; "Ruthenium-catalyzed Hydrogenation of Acids to Alcohols;" Journal of the American Chemical Society; 1955; vol. 77; Issue 14; pp. 3766-3768.
Matteoli et al.; "Structure and catalytic activity of phosphine-substituted ruthenium carbonyl carboxylates;" Journal of Organometallic Chemistry; 498; 1995; pp. 177-186.
https://www.ube-ind.co.jp/ube/en/news/2015/20160316_01.html Ube Industries Licenses DMC Technology and Agrees to Establish Joint Venture for High-Purity DMC.
vom Stein et al.; "Highly Versatile Catalytic Hydrogenation of Carboxylic and Carbonic Acid Derivatives using a Ru-Triphos Complex: Molecular Control over Selectivity and Substrate Scope;" J. Am. Chem. Soc.; 2014; 136; pp. 13217-13225.
Shuklov et al.; "Propane-1,2-diols from Dilactides, Oligolactides, or Poly-L-Lactic Acid (PLLA): From Plastic Waste to Chiral Bulk Chemicals;" Chem. Eur. J.; 2014; 20; pp. 957-960.
Spasyuk et al.; "Acceptorless Dehydrogenative Coupling of Ethanol and Hydrogenation of Esters and Imines;" Organometallics; 2012; 31; pp. 5239-5242.
Fan et al.; "Efficient Hydrogenation of Ethyl Lactate to 1,2-Propanediol over Ru—B/$TiO_2$ in Aqueous Solution;" Chemistry Letters; vol. 37, No. 8; 2008; pp. 852-853.
Zhang et al.; "Aqueous-phase hydrogenation of lactic acid to propylene glycol;" Applied Catalysis A: General; 2001; 219; pp. 89-98.
Adkins et al.; "The Hydrogenation of Esters to Alcohols at 25-150°;" Journal of the American Chemical Society; 1948; vol. 70; Issue 9; pp. 3121-3125.
Broadbent et al.; "Rhenium and Its Compounds as Hydrogenation Catalysts. III. Rhenium Heptoxide;" Journal of Organic Chemistry; 1959; vol. 24; Issue 12; pp. 1847-1854.
Hietala et al.; "Formic Acid"; Ullmann's Encyclopedia of Industrial Chemistry; vol. 16; 2012; Wiley-VCH Verlag GmbH & Co. KGaA, Weinheim; pp. 13-33.
Di Girolamo et al.; "Acidic and basic ion exchange resins for industrial applications;" Journal of Molecular Catalysis A: Chemical; 2001; 177; pp. 33-40.
Nørskov et al.; "Towards the computational design of solid catalysts;" Nature Chemistry; vol. 1; Apr. 2009; pp. 37-46.
Bielinski et al.; "Base-Free Methanol Dehydrogenation Using a Pincer-Supported Iron Compound and Lewis Acid Co-catalyst;" ACS Catal.; 2015; 5; pp. 2404-2415.
Fairweather et al.; "Homogeneous Hydrogenation of Fatty Acid Methyl Esters and Natural Oils under Neat Conditions;" Organometallics; 2015; 34; pp. 335-339.
Qu et al.; "Computational Mechanistic Study of Fe-Catalyzed Hydrogenation of Esters to Alcohols: Improving Catalysis by Accelerating Precatalyst Activation with a Lewis Base;" ACS Catal.; 2014; 4; pp. 4377-4388.
Notification of Transmittal of the International Search Report and the Written Opinion of the International Searching Authority dated Oct. 19, 2018 for International Application No. PCT/US2018/044482.
Notification of Transmittal of the International Search Report and the Written Opinion of the International Searching Authority dated Oct. 19, 2018 for International Application No. PCT/US2018/044485.
Notification of Transmittal of the International Search Report and the Written Opinion of the International Searching Authority dated Oct. 19, 2018 for International Application No. PCT/US2018/044476.
Notification of Transmittal of the International Search Report and the Written Opinion of the International Searching Authority dated Oct. 26, 2018 for International Application No. PCT/US2018/044518.

(56) References Cited

OTHER PUBLICATIONS

Pandey et al.; "Acceptorless Alcohol Dehydrogenation: A Mechanistic Perspective;" Proc. Natl. Acad. Sci., India, Sect. A Phys. Sci.; 2016; vol. 86; Issue 4; pp. 561-579.

Notification of Transmittal of the International Search Report and the Written Opinion of the International Searching Authority dated Oct. 26, 2018 for International Application No. PCT/US2018/044512.

Iranpoor et al.; "Silphos [$PCl_{3-n}(SiO2)_n$]: a heterogeneous phosphine reagent for formylation and acetylation of alcohols and amines with ethyl formate and acetate;" Tetrahedron Letters; 46; 2005; pp. 7963-7966.

Lane et al.; "Iron-Catalyzed Amide Formation from the Dehydrogenative Coupling of Alcohols and Secondary Amines;" Organometallics; 2017; 36; pp. 2020-2025.

Notification of Transmittal of the International Search Report and the Written Opinion of the International Searching Authority dated Oct. 26, 2018 for International Application No. PCT/US2018/044506.

Notice of Allowance dated Nov. 15, 2018 received in U.S. Appl. No. 16/043,317.

Notification of Transmittal of the International Search Report and the Written Opinion of the International Searching Authority dated Nov. 6, 2018 for International Application No. PCT/US2018/044521.

\* cited by examiner

SYNTHESIS OF GLYCOLS VIA TRANSFER HYDROGENATION OF ALPHA-FUNCTIONAL ESTERS WITH ALCOHOLS

CROSS REFERENCE TO RELATED APPLICATION

This application claims the benefit of Provisional Application 62/540,354 filed on Aug. 2, 2017 under 35 U.S.C. § 119(e)(1), the entire content of which is incorporated herein by reference.

FIELD OF THE INVENTION

The invention generally relates to the field of organic chemistry. It particularly relates to the catalytic transfer of hydrogen from alcohols to α-functional esters to form 1,2-diols.

BACKGROUND OF THE INVENTION

Conventional processes for preparing ethylene glycol (EG) and propylene glycol (PG) entail partial oxidation of ethylene or propylene followed by hydration of the resulting epoxides. More recently, hydrogenation of glycolate or oxalate esters has been proposed as alternative methods for preparing EG from alternative feedstock materials. These latter methods, however, suffer from one or more drawbacks, such as requiring the use of expensive precious or rare metal catalysts, high temperatures, and/or high hydrogen pressures.

Thus, there is a need in the art for a process for hydrogenating α-functional esters (such as glycolate esters, lactate esters, and oxalate esters) that does not suffer from these drawbacks.

The present invention addresses this need as well as others, which will become apparent from the following description and the appended claims.

SUMMARY OF THE INVENTION

The invention is as set forth in the appended claims.

Briefly, the invention provides a process for preparing a 1,2-diol. The process comprises contacting an ester of the formulas (IV) or (V):

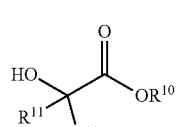
(IV)

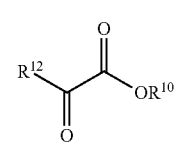
(V)

with an anhydrous $C_2$-$C_{12}$ alcohol in the presence of a catalyst of the formula (I):

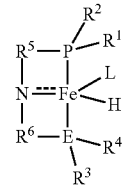
(I)

in a reactor at ambient pressure and elevated temperature for a time sufficient to form a 1,2-diol,
wherein
$R^1$ and $R^2$ are each independently an alkyl, aryl, alkoxy, aryloxy, dialkylamido, diarylamido, or alkylarylamido group having 1 to 12 carbon atoms;
$R^3$ and $R^4$ are each independently an alkyl or aryl group having 1 to 12 carbon atoms, if E is nitrogen;
$R^3$ and $R^4$ are each independently an alkyl, aryl, alkoxy, aryloxy, dialkylamido, diarylamido, or alkylarylamido group having 1 to 12 carbon atoms, if E is phosphorus;
$R^1$, $R^2$, and P may be connected to form a 5 or 6-membered heterocyclic ring;
$R^3$, $R^4$, and E may be connected to form a 5 or 6-membered heterocyclic ring;
$R^5$ and $R^6$ are each independently a $C_1$-$C_6$ alkylene or arylene group;
E is phosphorus or nitrogen;
L is a neutral ligand;
$R^{10}$ is an alkyl or aryl group having 1 to 20 carbon atoms;
$R^{11}$ is each independently hydrogen, or an alkyl or aryl group having 1 to 20 carbon atoms; and
$R^{12}$ is hydrogen, or an alkyl, aryl, alkoxy, or aryloxy group having 1 to 20 carbon atoms.

DETAILED DESCRIPTION OF THE INVENTION

It has been surprisingly discovered that certain iron-based catalysts are effective for the transfer hydrogenation of α-functional esters (such as glycolates or oxalates) to 1,2-diols in the presence of an alcohol as a sacrificial donor. The transfer hydrogenation (TH) uses a sacrificial alcohol (RR'CHOH) donor molecule instead of H2 gas as the reducing agent. Since no additional H2 pressure is required, these reactions can be run under ambient (or near ambient) pressure and at mild temperatures (e.g., ~100° C.).

Thus, the present invention provides a process for preparing a 1,2-diol. The process comprises contacting an ester of the formulas (IV) or (V):

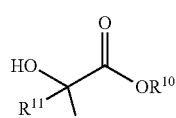
(IV)

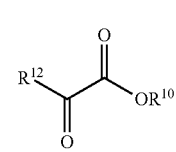
(V)

with an anhydrous $C_2$-$C_{12}$ alcohol in the presence of a catalyst of the formula (I):

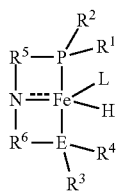

in a reactor at ambient pressure and elevated temperature for a time sufficient to form a 1,2-diol.

R1 and R2 in the formula (I) are each independently an alkyl, aryl, alkoxy, aryloxy, dialkylamido, diarylamido, or alkylarylamido group having 1 to 12 carbon atoms.

R3 and R4 in the formula (I) are each independently an alkyl or aryl group having 1 to 12 carbon atoms, if E is nitrogen.

R3 and R4 in the formula (I) are each independently an alkyl, aryl, alkoxy, aryloxy, dialkylamido, diarylamido, or alkylarylamido group having 1 to 12 carbon atoms, if E is phosphorus.

R5 and R6 in the formula (I) are each independently a C1-C6 alkylene or arylene group.

E in the formula (I) is phosphorus or nitrogen.

L in the formula (I) is a neutral ligand.

R1, R2, and P in the formula (I) may be connected to form a 5 or 6-membered heterocyclic ring.

R3, R4, and E in the formula (I) may be connected to form a 5 or 6-membered heterocyclic ring.

R10 in the formulas (IV) or (V) is an alkyl or aryl group having 1 to 20 carbon atoms.

R11 in the formula (IV) is each independently hydrogen, or an alkyl or aryl group having 1 to 20 carbon atoms.

R12 in the formula (V) is hydrogen, or an alkyl, aryl, alkoxy, or aryloxy group having 1 to 20 carbon atoms.

One or more of R1, R2, R3, and R4 may be substituted with one or more groups selected from ethers and amides. The substituents on R1, R2, R3, and R4, if any, may be the same or different.

Examples of ether groups include methoxy, ethoxy, isopropoxy, and the like.

Examples of amide groups include dimethylamido, diethylamido, diisopropylamido, and the like.

As used herein, the term "alkyl" refers to straight, branched, or cyclic alkyl groups. Examples of such groups include methyl, ethyl, n-propyl, isopropyl, n-butyl, sec-butyl, isobutyl, tert-butyl, n-pentyl, tert-pentyl, neopentyl, isopentyl, sec-pentyl, 3-pentyl, cyclopentyl, n-hexyl, isohexyl, cyclohexyl, and the like.

The term "aryl" generally refers to phenyl or naphthyl. But in connection with R10 and R11, the term "aryl" includes not only phenyl and naphthyl, but also other hydrocarbon rings containing alternating single and double bonds, such as indene, acenaphthylene, anthracene, phenanthrene, tryphenylene, pyrene, etc.

The term "alkylene" refers to a divalent alkyl group.

The term "arylene" refers to a divalent aryl group.

The term "alkoxy" refers to an —OR group, such as —OCH3, —OEt, —OiPr, —OBu, —OiBu, and the like.

The term "aryloxy" refers to an —OAr group, such as —OPh, —O(substituted Ph), —Onaphthyl, and the like.

The term "dialkylamido" refers to an —NR'R'' group, such as dimethylamido, diethylamido, diisopropylamido, and the like.

The term "diarylamido" refers to an —NAr'Ar'' group, such as diphenylamido.

The term "alkylarylamido" refers to an —NRAr group, such as methylphenylamido.

The term "neutral ligand" refers to a ligand with a neutral charge. Examples of neutral ligands include carbon monoxide, an ether compound, a phosphine compound, an amine compound, an amide compound, a nitrile compound, and an N-containing heterocyclic compound. Examples of neutral phosphine ligands include trimethylphosphine, tricyclohexylphosphine, triphenylphosphine, and the like. Examples of neutral amine ligands include trialkylamines, alkylarylamines, and dialkylarylamines, such as trimethylamine and N,N-dimethylanaline. Examples of neutral nitrile ligands include acetonitrile. Examples of neutral N-containing heterocyclic ligands include pyridine and 1,3-dialkyl- or diarylimidazole carbenes.

In one embodiment, R1, R2, R3, and R4 are all isopropyl. In another embodiment, R1, R2, R3, and R4 are all phenyl.

In one embodiment, R5 and R6 are both —(CH2CH2)-.

In one embodiment, E is phosphorus.

In various embodiments, the catalyst of the formula (I) has the formula (1c):

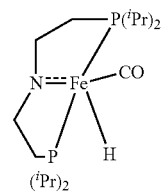

where $^iPr$ represents an isopropyl group.

The ester of the formulas (IV) or (V) useful in the present invention is not particularly limiting. In various embodiments, the ester includes a compound of the formula (IV). Such α-hydroxy carboxylic acid esters are sometimes referred to as glycolates. In various other embodiments, the ester includes a compound of the formula (V) where R12 is hydrogen, or an alkyl or aryl group. Such α-carbonyl carboxylic acid esters are sometimes referred to as glyoxalates. In yet various other embodiments, the ester includes a compound of the formula (V) where R12 is an alkoxy or aryloxy group. Such 1,2-diesters are sometimes referred to as oxalates.

Examples of the glycolates of the formula (IV) include methyl glycolate, ethyl glycolate, propyl glycolate, isopropyl glycolate, butyl glycolate, isobutyl glycolate, sec-butyl glycolate, 2-ethylhexyl glycolate, tert-butyl glycolate, cyclohexyl glycolate, phenyl glycolate, benzyl glycolate, naphthyl glycolate, methyl lactate, ethyl lactate, propyl lactate, isopropyl lactate, butyl lactate, isobutyl lactate, sec-butyl lactate, 2-ethylhexyl lactate, tert-butyl lactate, cyclohexyl lactate, benzyl lactate, methyl □-hydroxybutyrate, methyl □-hydroxyvalerate, methyl □-hydroxy-4-methylvalerate, methyl □-hydroxycaproate, methyl □-hydroxy-3-methylbutyrate, methyl □-hydroxy-3-methylvalerate, methyl □-hydroxy-3,3-dimethylbutyrate, methyl □-hydroxy-3,3-dimethylbutyrate, methyl mandelate, methyl □-hydroxy-3-phenyl propionate, methyl □-hydroxyisobutyrate, ethyl □-hydroxyisobutyrate, propyl □-hydroxyisobutyrate, isopropyl □-hydroxyisobutyrate, butyl □-hydroxyisobutyrate, methyl □-hydroxy-2-ethylbutyrate, ethyl □-hydroxy-2-ethylbutyrate, propyl □-hydroxy- 2-ethylbutyrate, ethylene glycol diglycolate, ethylene glycol glycolate, propylene glycol dilactate, propylene glycol monolactate, and the like. Glycolide or lactide (which are cyclic dimers of structural formula (IV)), oligomeric glycolates or lactates, and soluble low molecular weight polyesters of glycolic or lactic acid or copolyesters containing glycolic acid or lactic acid monomers in their compositions are further examples of the glycolate of the formula (IV).

Examples of the glyoxalates of the formula (V) include methyl glyoxalate, ethyl glyoxalate, propyl glyoxzalate, isopropyl glyoxalate, butyl glyoxalate, isobutyl glyoxalate, sec-butyl glyoxalate, tert-butyl glyoxalate, 2-ethylhexyl glyoxalate, phenyl glyoxalate, ethylene glycol mono- and diglyoxalate and mixtures thereof, methyl pyruvate, ethyl pyruvate, isopropyl pyruvate, butyl pyruvate, isobutyl pyruvate, sec-butyl pyruvate, tert-butyl pyruvate, phenyl pyruvate, propylene glycol mono- and dipyruvate and mixtures thereof, methyl phenylglyoxalate, ethyl phenylglyoxalate, propyl phenylglyoxalate, isopropyl phenylglyoxalate, butyl phenylglyoxalate, isobutyl phenylglyoxalate, sec-butyl phenylglyoxalate, tert-butyl phenylglyoxalate, mono- and diesters of phenylglyoxalic acid with 2-phenyl, and the like.

Examples of the oxalates of the formula (V) include dimethyl oxalate, diethyl oxalate, dipropyl oxalate, diisopropyl oxalate, dibutyl oxalate, diisobutyl oxalate, di-sec-butyl oxalate, bis(2-ethylhexyl)oxalate, di-tert-butyl oxalate, diphenyl oxalate, dicyclohexyl oxalate, dibenzyl oxalate, and low molecular weight oligomeric esters produced from condensation of oxalates, such as those above and varying amounts of ethylene glycol.

The 1,2-diol that can be produced using the process of the invention is not particularly limiting. Examples of such diols include 1,2-ethanediol, 1,2-propanediol, 1,2-butanediol, 1,2-pentanediol, 1,2-hexanediol, 2-methyl-1,2-propanediol, 1-phenyl-1,2-ethanediol, and 3-phenyl-1,2-propanediol.

The anhydrous alcohols useful in the present invention typically contain 2 to 12 carbon atoms. The alcohols may be linear, branched, or cyclic. Specific examples of suitable alcohols include ethanol, n-propanol, isopropanol, n-butanol, isobutanol, etc.

In various embodiments, the alcohol is ethanol. Anhydrous ethanol is commercially available in various grades, such as 200 proof, ≥99% of ethanol by volume, ≥99.5% of ethanol by volume, <1% of water by volume, <0.5% of water by volume, or <0.005% of water by volume. Any of these grades may be used in the TH reaction.

Preferably, the reaction mixture contains less than 1 wt %, less than 0.5 wt %, less than 0.4 wt %, less than 0.3 wt %, less than 0.2 wt %, less than 0.1 wt %, less than 0.05 wt %, less than 0.01 wt %, less than 0.005 wt %, or less than 0.001 wt % of water, based on the total weight of the reaction mixture. In one embodiment, the TH reaction is carried out in the absence of water.

The contacting step/TH reaction is preferably carried out using excess alcohol. For example, the molar ratio of the C2-C12 alcohol to the ester can be from 2:1 to 100:1, and all ranges in between including 2:1 to 50:1 and 10:1 to 30:1.

In one embodiment, the ester comprises methyl glycolate, the C2-C12 alcohol comprises ethanol, and the 1,2-diol comprises ethylene glycol.

In another embodiment, the ester comprises dimethyl oxalate, the $C_2$-$C_{12}$ alcohol comprises ethanol, and the 1,2-diol comprises ethylene glycol.

In yet another embodiment, the ester comprises methyl lactate, the C2-C12 alcohol comprises ethanol, and the 1,2-diol comprises propylene glycol.

The transfer hydrogenation process according to the invention can produce valuable by-products, such as ethyl acetate. The ethyl acetate may be isolated and purified by conventional methods and sold as a commodity chemical. Alternatively, the ethyl acetate can be hydrogenated at mild conditions and recycled as the reducing agent in an ambient pressure EG process.

The catalyst of the formula (I) may be prepared in multiple ways. For example, the catalyst may be formed in situ by introducing a pre-catalyst of the formulas (IIa) or (IIb):

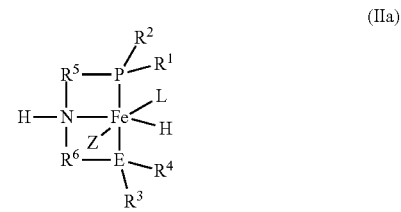

(IIa)

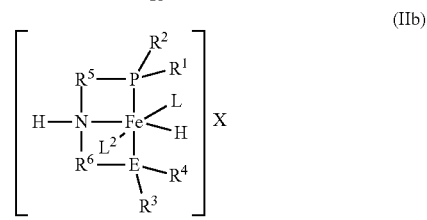

(IIb)

into the reactor and exposing the pre-catalyst to heat, an acid, a base, or combinations thereof to form the catalyst of the formula (I).

R1, R2, R3, R4, R5, R6, E, and L in the formulas (IIa) or (IIb) are as defined in formula (I).

Z in the formula (IIa) is R7 or X.

R7 is hydrogen or an alkyl or aryl group.

X is [BH4]- or a halide.

L2 in the formula (IIb) is a neutral ligand.

The alkyl or aryl group represented by R7 may contain from 1 to 12 carbon atoms.

The halides represented by X include chloride, bromide, and iodide. In one embodiment, X is chloride or bromide.

Examples of the neutral ligand L2 include an ether compound, an amide compound, a nitrile compound, and an N-containing heterocyclic compound.

In one embodiment, when X is a halide, the pre-catalyst is exposed to a base and optionally to heat to generate the catalyst.

In another embodiment, when X is [BH4]-, the pre-catalyst is exposed to heat, but optionally in the absence of a base, to generate the catalyst.

Unless the context clearly suggests otherwise, as used herein, the expression "in the absence of" means that the referenced component is not added from an external source (i.e., one that is independent of the reactants) or, if added, is not added in an amount that affects the TH reaction to an appreciable extent, for example, an amount that can change the yield of the corresponding alcohol by more than 10%, by more than 5%, by more than 1%, by more than 0.5%, or by more than 0.1%.

In various embodiments, the pre-catalyst of the formula (IIa) has the formula (1a):

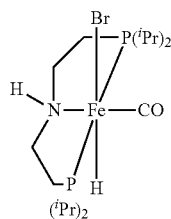

(1a)

where $^i$Pr represents an isopropyl group.

In various embodiments, the pre-catalyst of the formula (IIb) has the formula (1b):

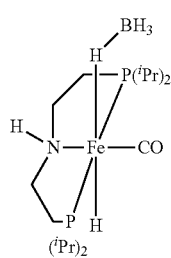

(1b)

where $^i$Pr represents an isopropyl group.

Alternatively, the catalyst of the formula (I) may be formed in situ by the steps of:

(a) introducing (i) an iron salt or an iron complex comprising the neutral ligand (L), (ii) a ligand of the formula (III):

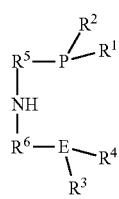

(III)

and (iii) optionally the neutral ligand (L) into the reactor to form a pre-catalyst mixture; and (b) optionally exposing the pre-catalyst mixture to heat, an acid, a base, or combinations thereof to form the catalyst of the formula (I).

R1, R2, R3, R4, R5, R6, and E in the formula (III) are as defined in formula (I).

Examples of iron salts suitable for making the catalyst of the formula (I) include [Fe(H2O)6](BF4)2, Fe(CO)5, FeCl2, FeBr2, FeI2, [Fe3(CO)12], Fe(NO3)2, FeSO4, and the like.

Iron complexes comprising the neutral ligand (L) may be made by methods known in the art and/or are commercially available.

Ligands of the formula (III) may be made by methods known in the art and/or are commercially available.

The heat employed for generating the catalyst is not particularly limiting. It may be the same as the heat used for the TH reaction. For example, the pre-catalyst or pre-catalyst mixture may be exposed to elevated temperatures, such as from 40 to 200° C., 40 to 160° C., 40 to 150° C., 40 to 140° C., 40 to 130° C., 40 to 120° C., 40 to 100° C., 80 to 160° C., 80 to 150° C., 80 to 140° C., 80 to 130° C., 80 to 120° C., or 80 to 100° C., to form the catalyst.

The acid for forming the catalyst is not particularly limiting. Examples of suitable acids include formic acid, $HBF_4$, $HPF_6$, $HOSO_2CF_3$, and the like.

The base for forming the catalyst is not particularly limiting. Both inorganic as well as organic bases may be used. Examples of suitable inorganic bases include Na, K, NaH, NaOH, KOH, CsOH, $LiHCO_3$, $NaHCO_3$, $KHCO_3$, $CsHCO_3$, $Li_2CO_3$, $Na_2CO_3$, $K_2CO_3$, $Cs_2CO_3$, and the like. Suitable organic bases include metal alkoxides and nitrogen-containing compounds. Examples of suitable metal alkoxides include alkali-metal $C_1$-$C_6$ alkoxides, such as LiOEt, NaOEt, KOEt, and KOt-Bu. In one embodiment, the base is sodium methoxide (NaOMe). In another embodiment, the base is sodium ethoxide (NaOEt). Examples of nitrogen-containing bases include trialkylamines, such as triethylamine.

Typically, a 1:1 molar equivalent of base to catalyst precursor is used to generate the catalyst. More than a 1:1 molar equivalent ratio may be used, e.g., a 2:1 ratio of base to catalyst precursor. However, using a large excess amount of base should be avoided, as it may suppress the formation of the 1,2-diol.

The conditions effective for forming the 1,2-diol include an elevated temperature. The temperature conducive for the TH reaction may range, for example, from 50 to 180° C., including all ranges in between, such as from 75 to 100° C.

Advantageously, the TH reaction may be conducted at ambient pressure or near ambient pressure. As noted, the process of the invention does not require a molecular hydrogen atmosphere. Therefore, preferably, the reaction is conducted in the absence of exogenous molecular hydrogen (H2).

Preferably, the contacting step/TH reaction is carried out in the absence of a base. Basic conditions during the reaction may tend to suppress the formation of the 1,2-diol.

The TH reaction may be conducted in the presence or absence of a solvent. In one embodiment, the contacting step/TH reaction is conducted in the presence of a solvent. In another embodiment, the contacting step/TH reaction is conducted in the absence of a solvent.

If desired, the TH reaction may be performed in common non-polar solvents, such as aliphatic or aromatic hydrocarbons, or in slightly polar, aprotic solvents, such as ethers. Examples of aliphatic solvents include pentanes and hexanes. Examples of aromatic solvents include benzene, xylenes, toluene, and trimethylbenzenes. Examples of ethers include tetrahydrofuran, dioxane, diethyl ether, and polyethers.

In various embodiments, the reaction is conducted in benzene, xylene(s), mesitylene, or toluene at atmospheric pressure.

If used, the solvent may be added in amounts of 1:1 to 100:1 or 1:1 to 20:1 (v/v), relative to the amount of the alcohol reactant.

The TH reaction can take place with catalyst loadings of 0 ppm (0.001 mol %). For example, the reaction may be carried out with catalyst loadings of 10 to 20,000 ppm (0.001 to 2 mol %), 10 to 15,000 ppm (0.001 to 1.5 mol %), 10 to 10,000 ppm (0.001 to 1 mol %), 10 to 1,000 ppm (0.001 to 0.1 mol %), or 10 to 500 ppm (0.01 to 0.05 mol %).

The process of the invention may be carried out in a batch or continuous mode. The reaction product(s) may be separated by conventional means, and the catalyst may be recycled.

The process according to the invention can produce the 1,2-diol with yields of at least 50%, at least 60%, at least 70%, at least 80%, at least 85%, at least 90%, at least 95%, or at least 99%. The reaction times in which these yields may be achieved include 20 hours or less, 18 hours or less, 16 hours or less, 12 hours or less, 10 hours or less, or 8 hour or less.

Low pressure hydrogenation of esters by TH allows for the production of glycols, such as EG and PG, with advantages in capital and operating costs, safety of operation, and flexibility for smaller scale, batch operations where high pressure facilities may not be readily available.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention unless otherwise specifically indicated.

EXAMPLES

General Experimental Information

Unless otherwise noted, all the organometallic compounds were prepared and handled under a nitrogen atmosphere using standard Schlenk and glovebox techniques. Anhydrous EtOH (200 proof) and toluene were purchased from Sigma Aldrich and stored with 4 Å molecular sieves. Both EtOH and toluene were freshly distilled prior to use. Dimethyl 1,4-cyclohexanedicarboxylate (DMCD, a mixture of cis and trans isomers, >90% purity) was purchased from Alfa Aesar and used without further purification. Compounds 1a-c have been previously reported in the literature. They were synthesized according to procedures that are slightly modified from the literature procedures.

Example 1

Synthesis of 1a [($^{iPr}$PNHP)Fe(H)(CO)(Br)]

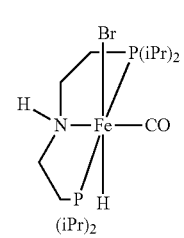

1a

In a glovebox, under a nitrogen atmosphere, a 200-mL oven-dried Schlenk flask was charged with complex [$^{iPr}$P-NHP]FeBr$_2$(CO) (850 mg, 1.545 mmol), NaBH$_4$ (60 mg, 1.545 mmol, 98% purity), and 100 mL of dry EtOH. The resulting yellow solution was stirred for 18 hours at room temperature and filtered through Celite. The filtrate was evaporated to dryness to obtain pure 1a (86% isolated yield). The $^1$H and $^{31}$P{$^1$H} NMR spectra of 1a agreed well with the reported values (see S. Chakraborty et al., J. Am. Chem. Soc. 2014, 136, 7869).

Example 2

Modified Synthesis of 1b [($^{iPr}$PNHP)Fe(H)(CO)(HBH$_3$)]

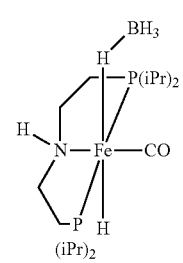

1b

In a glovebox, under a nitrogen atmosphere, a 200-mL oven-dried Schlenk flask was charged with complex [$^{iPr}$P-NHP]FeBr2(CO) (850 mg, 1.545 mmol), NaBH$_4$ (131 mg, 3.399 mmol, 98% purity), and 100 mL of dry EtOH. The resulting yellow solution was stirred for 18 hours at room temperature and filtered through Celite. The filtrate was evaporated to dryness to obtain pure 1b (84% isolated yield). The $^1$H and $^{31}$P{$^1$H} NMR spectra of 1 b agreed well with the reported values (see S. Chakraborty et al., J. Am. Chem. Soc. 2014, 136, 7869).

Example 3

Modified Synthesis of 1c [($^{iPr}$PNP)Fe(H)(CO)]

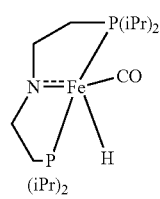

1c

In a glovebox, under a nitrogen atmosphere, a 200-mL oven-dried Schlenk flask was charged with complex 1b (500 mg, 1.06 mmol), NaOtBu (106 mg, 1.07 mmol, 97% purity), and 60 mL of dry THF. Immediately, a deep red solution resulted, which was stirred for an additional 30 minutes at room temperature. After that, the solvent was removed under vacuum, and the desired product was extracted into pentane and filtered through a plug of Celite to remove NaBr. The resulting filtrate was evaporated under vacuum to afford pure 1c (76% isolated yield). The $^1$H and $^{31}$P{$^1$H} NMR spectra of 1c agreed well with the reported values (see S. Chakaraborty et al., *J. Am. Chem. Soc.* 2014, 136, 8564).

Example 4

Iron-Catalyzed Transfer Hydrogenation of Methyl Glycolate in the Presence of EtOH Under an inert atmosphere, an oven-dried 200-mL thick-wall Schlenk tube equipped with a stir-bar was charged with compound 1c (0.1 mmol), methyl glycolate (0.01 mol, 0.91 g, 98% pure), anhydrous EtOH (0.2 mol, 11.7 mL), and 20 mL of anhydrous toluene. The resulting mixture was heated to 100° C. for ~16 h using an oil-bath. After ~16 h, the brown colored solution was cooled to room temperature, volatiles were carefully vented inside the hood, and the resulting liquid was analyzed by gas chromatography.

Under these conditions, 63.1% of methyl glycolate was converted to yield 51.7% of ethylene glycol (EG). EtOAc, MeOH, and trace amounts of methyl formate were also observed as other volatile byproducts.

Example 5

Iron-Catalyzed Transfer Hydrogenation of Dimethyl Oxalate in the Presence of EtOH Under an inert atmosphere, an oven-dried 200-mL thick-wall Schlenk tube equipped with a stir-bar was charged with compound 1c (0.1 mmol), dimethyl oxalate (0.01 mol, 1.2 g, 99% pure), anhydrous EtOH (0.2 mol, 11.7 mL), and 20 mL of anhydrous toluene. The resulting mixture was heated to 100° C. for ~16 h using an oil-bath. After ~16 h, the brown colored solution was cooled to room temperature, volatiles were carefully vented inside the hood, and the resulting liquid was analyzed by gas chromatography.

Under these conditions, 47.8% of dimethyl oxalate was converted to yield 18.4% of ethylene glycol (EG) and 23.5% of methyl glycolate. EtOAc, MeOH, and trace amounts of methyl formate were also observed as other volatile byproducts.

In the specification, there have been disclosed certain embodiments of the invention and, although specific terms are employed, they are used in a generic and descriptive sense only and not for purposes of limitation, the scope of the invention being set forth in the following claims.

We claim:

1. A process for preparing a 1,2-diol, the process comprising contacting an ester of the formulas (IV) or (V):

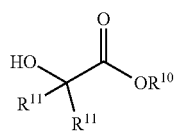
(IV)

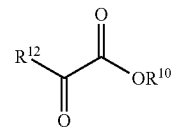
(V)

with an anhydrous $C_2$-$C_{12}$ alcohol in the presence of a catalyst of the formula (I):

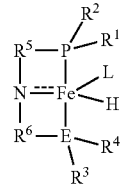
(I)

in a reactor at ambient pressure and elevated temperature for a time sufficient to form a 1,2-diol, wherein $R^1$ and $R^2$ are each independently an alkyl, aryl, alkoxy, aryloxy, dialkylamido, diarylamido, or alkylarylamido group having 1 to 12 carbon atoms;

$R^3$ and $R^4$ are each independently an alkyl or aryl group having 1 to 12 carbon atoms, if E is nitrogen;

$R^3$ and $R^4$ are each independently an alkyl, aryl, alkoxy, aryloxy, dialkylamido, diarylamido, or alkylarylamido group having 1 to 12 carbon atoms, if E is phosphorus;

$R^1$, $R^2$, and P may be connected to form a 5 or 6-membered heterocyclic ring;

$R^3$, $R^4$, and E may be connected to form a 5 or 6-membered heterocyclic ring;

$R^5$ and $R^6$ are each independently a $C_1$-$C_6$ alkylene or arylene group;

E is phosphorus or nitrogen;

L is a neutral ligand;

$R^{10}$ is an alkyl or aryl group having 1 to 20 carbon atoms;

$R^{11}$ is each independently hydrogen, or an alkyl or aryl group having 1 to 20 carbon atoms; and $R^{12}$ is hydrogen, or an alkyl, aryl, alkoxy, or aryloxy group having 1 to 20 carbon atoms.

2. The process according to claim 1, wherein the catalyst is formed by introducing a pre-catalyst of the formulas (IIa) or (IIb):

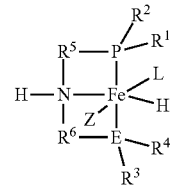
(IIa)

13

-continued

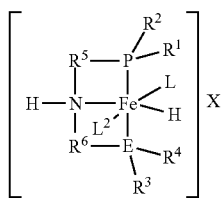

(IIb)

into the reactor and exposing the pre-catalyst to heat, an acid, a base, or combinations thereof; and
wherein
$R^1$, $R^2$, $R^3$, $R^4$, $R^5$, $R^6$, E, and L are as defined in formula (I);
Z is $R^7$ or X;
$R^7$ is hydrogen or an alkyl or aryl group;
X is $[BH_4]^-$ or a halide; and
$L^2$ is a neutral ligand.

3. The process according to claim 1, wherein the catalyst is formed by:
(a) introducing (i) an iron salt or an iron complex comprising the neutral ligand (L), (ii) a ligand of the formula (III):

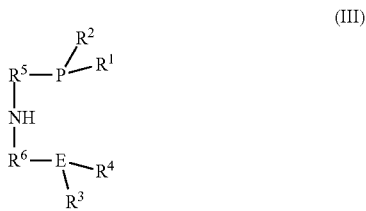

(III)

and (iii) optionally the neutral ligand (L) into the reactor to form a pre-catalyst mixture; and
(b) optionally exposing the pre-catalyst mixture to heat, an acid, a base, or combinations thereof;
wherein $R^1$, $R^2$, $R^3$, $R^4$, $R^5$, $R^6$, and E are as defined in formula (I).

4. The process according to claim 1, wherein one or more of $R^1$, $R^2$, $R^3$, and $R^4$ are substituted with one or more groups selected from ethers and amides.

5. The process according to claim 1, wherein $R^1$, $R^2$, $R^3$, and $R^4$ are each independently a methyl, ethyl, propyl, isopropyl, butyl, pentyl, isopentyl, cyclopentyl, hexyl, cyclohexyl, or phenyl group.

6. The process according to claim 5, wherein each of $R^1$, $R^2$, $R^3$, and $R^4$ is isopropyl.

7. The process according to claim 5, wherein each of $R^1$, $R^2$, $R^3$, and $R^4$ is phenyl.

8. The process according to claim 1, wherein each of $R^5$ and $R^6$ is —$(CH_2CH_2)$—.

9. The process according to claim 1, wherein E is phosphorus.

10. The process according to claim 1, wherein L is carbon monoxide, a phosphine, an amine, a nitrile, or an N-containing heterocyclic ligand.

11. The process according to claim 2, wherein $L^2$ is an ether, an amide, a nitrile, or an N-containing heterocyclic ligand.

12. The process according to claim 1, wherein the contacting step is conducted at a temperature of 50 to 180° C.

13. The process according to claim 1, wherein the contacting step is conducted at a temperature of 75 to 100° C.

14. The process according to claim 1, wherein the contacting step is conducted in the absence of exogenous molecular hydrogen ($H_2$).

15. The process according to claim 1, wherein the contacting step is conducted in the presence of a solvent.

16. The process according to claim 2, wherein the base is a metal alkoxide or a nitrogen-containing compound.

17. The process according to claim 16, wherein the base is sodium methoxide, sodium ethoxide, or triethylamine.

18. The process according to claim 1, wherein the molar ratio of the $C_2$-$C_{12}$ alcohol to the ester ranges from 2:1 to 100:1.

19. The process according to claim 1, wherein the $C_2$-$C_{12}$ alcohol comprises ethanol, isopropanol, or isobutanol.

20. The process according to claim 1, wherein the ester is a compound of the formula (IV).

21. The process according to claim 1, wherein the ester is a compound of the formula (V).

22. The process according to claim 20, wherein the ester comprises methyl glycolate, the $C_2$-$C_{12}$ alcohol comprises ethanol, and the 1,2-diol comprises ethylene glycol.

23. The process according to claim 20, wherein the ester comprises methyl lactate, the $C_2$-$C_{12}$ alcohol comprises ethanol, and the 1,2-diol comprises propylene glycol.

24. The process according to claim 21, wherein the ester comprises dimethyl oxalate, the $C_2$-$C_{12}$ alcohol comprises ethanol, and the 1,2-diol comprises ethylene glycol.

* * * * *